US008945602B2

(12) United States Patent
Freeman et al.

(10) Patent No.: US 8,945,602 B2
(45) Date of Patent: *Feb. 3, 2015

(54) POROUS PHOTONIC CRYSTALS FOR DRUG DELIVERY TO THE EYE

(71) Applicant: The Regents of the University of California, Oakland, CA (US)

(72) Inventors: William Freeman, Del Mar, CA (US); Michael J. Sailor, La Jolla, CA (US); Lingyun Cheng, San Diego, CA (US); Frederique Cunin, Montpellier (FR); Emily Anglin, San Diego, CA (US); Yang Yang Li, Hong Kong (HK)

(73) Assignee: The Regents of the University of California, Oakland, CA (US)

( * ) Notice: Subject to any disclaimer, the term of this patent is extended or adjusted under 35 U.S.C. 154(b) by 106 days.

This patent is subject to a terminal disclaimer.

(21) Appl. No.: 13/854,039

(22) Filed: Mar. 29, 2013

(65) Prior Publication Data

US 2013/0224302 A1 Aug. 29, 2013

Related U.S. Application Data (63) Continuation of application No. 11/665,557, filed as application No. PCT/US2005/039177 on Oct. 31, 2005.

(60) Provisional application No. 60/623,409, filed on Oct. 29, 2004.

(51) Int. Cl.
| | |
|---|---|
| *A61K 47/02* | (2006.01) |
| *A61K 38/00* | (2006.01) |
| *A61K 31/122* | (2006.01) |
| *A61K 9/14* | (2006.01) |
| *A61K 9/00* | (2006.01) |
| *A61F 9/00* | (2006.01) |
| *A61K 47/24* | (2006.01) |

(52) U.S. Cl.
CPC ............ *A61K 9/0048* (2013.01); *A61F 9/0017* (2013.01); *A61K 9/0051* (2013.01); *A61K 47/24* (2013.01)
USPC ........... 424/427; 424/429; 424/489; 424/499; 424/94.63; 514/1.1; 514/20.8; 514/691

(58) Field of Classification Search
CPC ... A61K 9/0048; A61K 9/0051; A61K 9/141; A61K 31/122; A61K 38/49; A61K 38/00
USPC ........ 424/489, 427, 429, 499, 94.63; 514/1.1, 514/20.8, 691
See application file for complete search history.

(56) References Cited

U.S. PATENT DOCUMENTS

| | | | |
|---|---|---|---|
| 2,674,743 | A | 4/1954 | Gaiser et al. |
| 3,828,777 | A | 8/1974 | Ness |
| 5,242,950 | A | 9/1993 | Hastings |
| 6,322,865 | B1 | 11/2001 | Winget et al. |
| 6,666,214 | B2 | 12/2003 | Canham |
| 6,770,480 | B1 | 8/2004 | Canham |
| 6,929,950 | B2 | 8/2005 | Canham et al. |
| 7,332,339 | B2 | 2/2008 | Canham |
| 7,638,137 | B2 | 12/2009 | Chauhan et al. |
| 7,763,277 | B1 | 7/2010 | Canham et al. |
| 8,088,401 | B2 | 1/2012 | Saffie et al. |
| 8,097,236 | B2 | 1/2012 | Aston et al. |
| 8,147,864 | B2 | 4/2012 | Canham et al. |
| 8,293,630 | B2 | 10/2012 | Dunkley et al. |
| 8,303,975 | B2 | 11/2012 | Canham et al. |
| 8,313,761 | B2 | 11/2012 | Canham et al. |
| 8,318,194 | B2 | 11/2012 | Canham et al. |
| 8,361,491 | B2 | 1/2013 | Canham et al. |
| 2002/0156274 | A1 | 10/2002 | Terfloth |
| 2003/0060878 | A1 | 3/2003 | Shadduck et al. |
| 2003/0146109 | A1 | 8/2003 | Sailor et al. |
| 2004/0052867 | A1 | 3/2004 | Canhann |
| 2004/0244889 | A1 | 12/2004 | Sailor et al. |
| 2005/0009374 | A1 | 1/2005 | Gao et al. |
| 2005/0042764 | A1 | 2/2005 | Sailor et al. |
| 2005/0101026 | A1 | 5/2005 | Sailor et al. |
| 2005/0181049 | A1 | 8/2005 | Dong et al. |
| 2006/0236436 | A1 | 10/2006 | Li et al. |
| 2006/0255008 | A1 | 11/2006 | Link et al. |

(Continued)

FOREIGN PATENT DOCUMENTS

| | | |
|---|---|---|
| AU | 753542 | 2/2000 |
| CA | 2228426 | 2/1997 |

(Continued)

OTHER PUBLICATIONS

Madou, Marc J. "Fundamentals of Microfabrication: The Science of Miniaturization", Second Edition, 2002, pp. 228-232.
Sailor, Michael et al. "Biomolecular screening with encoded porous-silicon photonic crystals", Nature Materials, vol. 1, published online Sep. 2, 2002, pp. 39-41.
Non-Final Office Action, U.S. Appl. No. 11/665,557, Oct. 14, 2011.
Final Office Action, U.S. Appl. No. 11/665,557, May 3, 2012.
Non-Final Office Action, U.S. Appl. No. 11/665,557, Nov. 6, 2013.
Final Office Action, U.S. Appl. No. 11/665,557, Apr. 28, 2014.

(Continued)

*Primary Examiner* — Richard Schnizer
*Assistant Examiner* — Alma Pipic
(74) *Attorney, Agent, or Firm* — Joseph R. Baker, Jr.; Gavrilovich Dodd & Lindsey LLP (57) ABSTRACT

A minimally invasive controlled drug delivery system for delivering a particular drug or drugs to a particular location of the eye, the system including a porous film template having pores configured and dimensioned to at least partially receive at least one drug therein, and wherein the template is dimensioned to be delivered into or onto the eye.

11 Claims, 3 Drawing Sheets

(56) References Cited

U.S. PATENT DOCUMENTS

| | | |
|---|---|---|
| 2007/0154522 A1 | 7/2007 | Chow et al. |
| 2009/0208556 A1 | 8/2009 | Freeman et al. |
| 2013/0064965 A1 | 3/2013 | Canham et al. |

FOREIGN PATENT DOCUMENTS

| | | |
|---|---|---|
| CA | 2368679 | 11/2000 |
| CA | 2228426 C | 2/2008 |
| CA | 2328996 C | 12/2012 |
| CN | 99809028 | 8/2001 |
| CN | 00809693.7 | 8/2002 |
| EP | 842113 A | 5/1998 |
| EP | 1407764 A1 | 4/2004 |
| EP | 1071398 B1 | 5/2004 |
| EP | 1776949 A2 | 4/2007 |
| EP | 2269574 A2 | 1/2011 |
| GB | 9909996.2 | 5/1999 |
| NZ | 509142 | 1/2004 |
| NZ | 515189 | 5/2004 |
| WO | 9706101 | 2/1997 |
| WO | 00/05339 | 2/2000 |
| WO | 0066190 | 11/2000 |
| WO | 0215863 A1 | 2/2002 |
| WO | 03067231 A1 | 8/2003 |
| WO | 2004071949 | 8/2004 |
| WO | 2004071949 A2 | 8/2004 |
| WO | 2005034725 | 4/2005 |
| WO | 2006044957 A2 | 4/2006 |
| WO | 2006/050221 A2 | 5/2006 |
| WO | 2009/009563 A9 | 1/2009 |

OTHER PUBLICATIONS

Annalisa, Giro, Office Action issued in European Patent Application No. 05819498.6, Jan. 28, 2014.

Li, Yang Yang, et al., "Polymer replicas of photonic porous silicon for sensing and drug delivery applications," Science, 2003, vol. 299, pp. 2045-2047.

Han, Jung Hee, International Search Report and Written Opinion, Date of Mailing of Search Report: Jun. 22, 2009, International Application No. PCT/US08/69474, 14 pages.

Ghali, Isis A., International Search Report and Written Opinion, Date of Mailing of Report: May 23, 2007, International Application No. PCT/US05/39177, 6 pages.

Wittmann-Regis, Agnes, International Preliminary Report on Patentability and Written Opinion, Date of Issuance of Report: Jun. 26, 2007, International Application No. PCT/US05/39177, 4 pages.

Lai et al., "A Mesoporous Silica Nanosphere-Based Carrier System with Chemically Removable CdS Nanoparticle Caps for Stimuli-Responsive Controlled Release of Neurotransmitters and Drug Molecules," Journal of American Chemical Society, 125, pp. 4451-4459, published on web Mar. 20, 2003.

Cohen et al., "Microfabrication of Silicon-Based Nanoporous Particulates for Medical Applications," Biomedical Microdevices, 5:3, pp. 253-259, published 2003.

Mortemousque et al., S/e-PTFE Episcleral Buckling Implants: An Experimental and Histophathologic Study, Journal of Biomedical Materials Research, 63, pp. 686-691, Published 2002.

Baharlou, Simin., International Preliminary Report on Patentability and Written Opinion, International Application No. PCT/US2006/069474, Date of Issuance of this Report: Jan. 12, 2010.

Harvey, Michael, Examination Report, New Zealand Application No. 583120, Date of Report: Nov. 12, 2010.

Liu, Huiying, The First Office Action, Chinese Application No. 200880106417.9, Date of Mailing: Mar. 9, 2011.

Anglin et al., "Engineering the chemistry and nanostructure of porous silicon fabry-perot films for loading and release of a steroid," Langmuir, Oct. 2004, pp. 11264-11269, vol. 20, No. 25.

Charney et al., "Inclusion of ibuprofen in mesoporous templated silica: drug loading and release property," European J. of Pharm. and Biopharm., May 2004, pp. 533-540, vol. 57, No. 3.

Giro, Annalisa, Extended European Search Report, European Patent Office, May 14, 2012, PCT/US2005039177.

Rysiakiewicz-Pasek et al.,, "Effect of potassium nitrate treatment on the adsorption properties of silica porous glasses," J. of Non-Crystalline Solids, Oct. 2004, pp. 260-264, vol. 345-346.

POROUS PHOTONIC CRYSTALS FOR DRUG DELIVERY TO THE EYE

CROSS REFERENCE TO RELATED APPLICATIONS

This application is a continuation of U.S. patent application Ser. No. 11/665,557, filed Apr. 16, 2007, which is a U.S. National Stage Application of International Application No. PCT/US2005/039177, filed Oct. 31, 2005, which application claims priority to U.S. Provisional Application No. 60/623, 409, filed Oct. 29, 2004, the disclosures of which are incorporated herein by reference.

STATEMENT OF GOVERNMENT SPONSORED RESEARCH

This invention was made with Government support under grant No. F49620-02-1-0288 awarded by the Air Force Office of Scientific Research (AFOSR), under grant No. EY07366 awarded by the National Institutes of Health, and under grant No. DMR-0503006 awarded by the National Science Foundation. The U.S. Government has certain rights in this invention.

FIELD OF THE INVENTION

A field of the invention is nanostructure synthesis. Other fields of the invention include drug delivery, bioimplant materials and self-reporting bioresorbable materials.

BACKGROUND OF THE INVENTION

Diseases of the eye are numerous and frequently difficult to treat effectively. For example, some areas of the eye are difficult to reach with systemic medications, while medications applied topically tend to be transient and require numerous and repeated applications. Surgical treatment of still other diseases is invasive and often problematic as well, with many patients ineligible for surgical treatment.

For example, intraocular diseases, such as age-related macular degeneration (ARMD) and choroidal neovascularization (CNV), are the leading cause of irreversible vision loss in the United States, and yet currently available treatments for subfoveal CNV, which comprise the majority of CNV cases, are associated with only marginal visual improvement and outcomes. As few as one quarter of patients with CNV associated with ARMD are laser eligible, and at least half of those treated experience recurrence of the disease with poor visual outcomes. Similarly, photodynamic therapy using verteporfin is only useful for the small minority of patients with vessels that are angiographically classified as "predominantly classic," and even then the visual outcomes of such treatments are disappointing.

Pharmacologic therapy using local drug delivery or systemic drug delivery is also being investigated using drugs that are antiangiogenic. Such drugs include angiostatic steroids, metalloproteinase inhibitors and VEGF binding drugs. However, the problem common to all of these promising drugs is the transient nature of the therapeutic level requires frequent intravitreal injection.

Nonspecific uveitis is another devastating eye disease that affects millions of people in the world. Uveitis produces a wide spectrum of inflammation of most parts of the eye and chronic uveitis can be devastating in adults and children. Surgically implanted steroids have shown that high intraocular doses for sustained times are extremely beneficial to choronic uveitis patients, but this implant has surgically related side effects.

Intravitreal injection is being used in clinical trials of therapeutic agents, but pose a risk of infection that is estimated to be 0.5% per injection. Due to the short vitreous half-life of most small molecules after intravitreal injection, frequent injection is needed, which significantly increases the chance of intraocular infection.

Delivery of drugs into vitreous via liposomes or slow release crystalline lipid prodrugs extend the drug vitreous half-life, but traditional liposomes or self-assembling liposomes often decrease vitreous clarity when used, can not be easily customized to release drugs with different physicochemical properties, and do not "report" drug release information.

Extraocular diseases are also difficult to treat because, for example, eye drops applied topically require repeated and frequent doses.

SUMMARY OF THE INVENTION

The invention provides minimally invasive controlled drug delivery systems and methods for use in delivery of a particular drug or drugs to the eye that include porous film or porous film particles having pores configured and dimensioned to at least partially receive at least one drug therein. Embodiments include devices and methods for treating intraocular diseases where porous film particles impregnated with a particular drug are sized and configured to permit intraocular injection of the loaded porous film particles. Other embodiments include devices and methods for treating extraocular diseases, where one of a porous film, biodegradable polymer replica or porous Si-polymer composite impregnated with a particular drug is configured to contact a portion of the eye, such as the ocular surface or retrobulbar surface, and controllably release the drug for surface delivery of the drug. Advantageously, release of the drug is also monitorable such that the amount of drug remaining in the porous substrate can be accurately quantified.

DETAILED DESCRIPTION OF THE INVENTION

The invention recognizes and addresses an important and unmet medical need for a minimally invasive, controllable and monitorable drug delivery system and methods of using the system that would enable long acting local treatment of both extraocular and intraocular diseases.

For intraocular diseases, such as glaucoma, age-related macular degeneration (ARMD), choroidal neovascularization (CNV), uveitis and others, drug delivery to the vitreous, retina, and choroid is a challenging task due to the formidable obstacles posed by the blood-retinal barrier and the tight junctions of the retinal pigment epithelium. Only small fractions of drug administered systemically reach the target, requiring large and potentially toxic doses when delivered systemically. Another challenge to retinal drug delivery is the fact that drug levels should be sustained for prolonged periods at the target site. This is difficult using intravitreal injections because the short half-life of most intravitreal injectable drugs. Intraocular implants have provided sustained vitreoretinal drug levels for treating certain retinal diseases. However, this route demands intraocular surgery that is known to cause intraocular complications when placing and replacing the implant.

For extraocular diseases, such as viral keratitis, chronic allergic conjunctivitis, and scleritis, some of the same problems persist. Systemic administration of drug requires potentially toxic doses, and topical treatments have a short half-life, requiring numerous and frequent doses.

Separately, photonic crystals have widespread application in optoelectronics, chemical and biological sensors, high-throughput screening, and drug delivery applications. These photonic crystals are especially advantageous because of the relative ease with which the optical properties, pore size, and surface chemistry can be manipulated. Moreover, position, width, and intensity of spectral reflectivity peaks may be controlled by the current density waveform and solution composition used in the electrochemical etch, thus rendering possible the preparation of films of porous Si photonic crystals that display any color within the visible light band with high color saturation, which is a desirable feature for information displays. Traditional methods of intraocular drug delivery include the use of liposomes or self-assembling liposomes, which often decrease vitreous clarity when used, cannot be easily customized to release drugs with different physicochemical properties, and do not "report" drug release information.

Advantageously, the invention provides devices and methods for treating both intraocular and extraocular diseases that promote sustained release of a pharmacalogical candidate, or drug, that is impregnated on nanostructured silicon, such as Si, $SiO_2$, Si/polymer or $SiO_2$/polymer composite.

Preferred devices and methods are also self-reporting such that drug release and quantity remaining are susceptible to monitoring. Embodiments of the invention include minimally invasive, self-reporting, controlled delivery systems for delivering a drug or drugs to surfaces of the eyes, both the ocular surface (cornea and conjunctiva) and the scleral surface, as well as intraocular portions of the eye, including the retina, choroids, lens, ciliary body, anterior chamber, and vitreous.

A first preferred embodiment includes injection of porous microscopic nanostructured silicon particles impregnated with a particular drug or drugs. While the invention contemplates use of numerous porous microscopic particles, preferred particles include porous silicon or silicon dioxide particles (so called, "smart dust"), which are prepared with a designed nanostructure that allows maintenance of sustained intraocular therapeutic drug levels with minimal invasiveness and elimination of systemic side effects. In addition to configuring the nanostructure to suit individual applications, the invention also contemplates chemically modifying the particles and the particular drug or drugs to tune and control release profiles of the particles. intraocular injection allows monitoring of drug levels non-invasively.

Porous silicon is especially advantageous in that porous silicon films have a large free volume (typically 50-800), and thus a high capacity for a drug can be custom designed at the nanoscale to deliver one or more drugs at a variety of customizable release rates with multiple drugs, and the photonic properties of a nanostructured material as a means to non-invasively determine the rate and amount of drug delivered has never been tested in the eye. The porous silicon photonic crystal particles are impregnated with a particular drug, and subsequently introduced into the retina, choroids, lens ciliary body, anterior chamber, and vitreous of the eye via injection. For details of coded photonic particles and methods of preparing same, see published U.S. application Ser. Nos.: 20050101026 entitled, "Photoluminescent polymetalloles as chemical sensors," 20050042764 entitled, "Optically encoded particles," 20050009374 entitled, "Direct patterning of silicon by photoelectrochemical etching," 20040244889. entitled, "Porous silicon-based explosive," and 20030146109 entitled, "Porous thin film time-varying reflectivity analysis of samples." The "smart dust" photonic crystal particles may be optimized. for intravitreal delivery of one or more of a vast array of drugs such as, for example, pigment epithelium derived factor (PEDF), an 8-mer peptide fragment of urokinase (uPA), dexamethasone, and a host of other drugs, small molecules, proteins, peptides and nucleic acids. These smart dust photonic crystals may be impregnated with drugs by either trapping one or more of the drugs in porous Si smart dust, or second, the pores themselves may be chemically modified to bind the candidate drug.

Photonic crystals are produced from porous silicon and porous silicon/polymer composites, or porous Si film or polymer replica or Si-polymer composite may be generated as a sheet for an exoplant. Pulsed electrochemical etching of a silicon chip produces a multilayered porous nanostructure. A convenient feature of porous Si is that the average pore size can be controlled over a wide range by appropriate choice of current, HF concentration, wafer resistivity, and electrode configuration used in the electrochemical etch. This tunability of the pore dimensions, porosity, and surface area is especially advantageous.

The porous film is lifted off the silicon substrate, and it is then broken into micron-sized particles having a size conducive to intraocular injection. For example, in one preferred embodiment, the micron-sized particles are sized and configured such that they may be injected into the eye with a 25 or 27-gauge needle. The particles act as one-dimensional photonic crystals, displaying an optical reflectivity spectrum that is determined by the waveform used in the electrochemical etch. This spectrum acts as an optical barcode that can be observed through human tissue using, for example, an inexpensive CCD spectrometer and a white light source. For the drug delivery methods and systems of the invention, a drug is impregnated and trapped in the pores, and the optical code may be used to report on the release rate of the drug in the vitreous. In this manner, the amount of drug may be quantified to determine how much remains within the particles, and whether administration of additional doses are necessary.

Advantageously, the optical interference spectrum used in particle identification can be measured with inexpensive and portable instrumentation (a CCD spectrometer or a diode laser interferometer). Removal of the drug from the pores is predicted to result in a change in the refractive index of the porous film and will be observed as a wavelength shift in the spectral code of the dust particle. Characteristic color changes are thus indicative. of drug quantity remaining. in the pores. Thus, the term photonic crystal is used for the film that has been machined and sized to small crystals for intraocular injection.

For intraocular delivery of drugs, a doctor or clinician may look through the iris of the eye and into the clear part of the eye to observe the colors of the injected particles. In this manner, the amount of drug remaining or the degree to which the particles have dissolved may be monitored, which in turns permits the doctor or clinician to forecast the length of time before the particles completely dissolve, and to predict when the patient may need subsequent injections.

By way of example only, binding and release of a DNA 16-mer, IgG (using a Protein A receptor) and biotinylated bovine serum albumin (using a streptavidin receptor) have been demonstrated using this methodology. The high surface area and optical interferometric means of detection lead to very high sensitivity for many of these systems, and the fact that the materials are constructed from single crystal Si substrates means they can be readily prepared using Si microfabrication technologies.

In addition to having pore characteristics (thickness, pore size, and porosity) that may be controlled by the current density, duration of the etch cycle, and etchant solution composition, the porous silicon film may also be used as a template to generate an imprint of biologically compatible or bioresorbable materials. Both the porous silicon film and/or its imprint possess a sinusoidally varying porosity gradient, providing sharp features in the optical reflectivity spectrum that have been used to monitor the presence or absence of chemicals trapped in the pores. It has been shown that the particles (smart dust) made from the porous silicon films by mechanical grinding or by ultrasonic fracture still carry the optical reflectivity spectrum. These porous silicon particles can be oxidized to increase stability and injected into animal eyes without toxicity to the intraocular tissues since silica is a mineral needed by the body for building bones and connective tissue. Previous studies have demonstrated the biocompatibility of porous Si in vitro and in animal models.

Other preferred embodiment include use of a porous silicon or silicon/polymer composite at a particular location of the eye, or using the porous silicon or silicon/polymer composite as a template to generate other biologically compatible or biologically resorbable materials for similar use. Biodegradable polymer imprints may be made from porous silicon templates, which may be used as drug delivery contact lenses or implants at an appropriate location of the eye, including the ocular surface and retrobulbar surface.

A second preferred embodiment of the invention include drug(s) impregnated in porous films configured to be worn or attached on the front of the eye. A contact lens formed of impregnated porous thin film material, for example, comprises and embodiment of the invention. While the second embodiment encompasses a contact lens, it also contemplates other similarly curved solid template correspondingly shaped with a front surface of the eye, as well as being configured to join the eye at the sclera as an episcleral plaque. The particular drug or drugs to be used with the polymer imprint may be added to the imprint solution prior to casting or engineered into the pores of the imprint after casting.

Accordingly, the second embodiment of the invention provides a system and method of drug delivery wherein porous silicon films can be variously modified to be a long-lasting intraocular drug delivery vehicle to carry various therapeutic compounds. In addition, biodegradable porous polymer imprints made from porous silicon templates can be used as a drug delivery implant to be placed at an appropriate location in the eye. The drug can be added into the imprint solution before casting or engineered into the pores after casting.

For the extraocular drug delivery, the emphasis on optical reporting declines. With the episcleral plaque, for example, delivery is retrobulbar, and it is not as easy to use an optical instrument to "read" these films. In this retrobulbar embodiment, the ability of the nanostructure to set the rate of dissolution or drug release. Because the electrochemical process used to construct porous Si can control the nanostructure to such a precise degree, precise control of the dissolution and/or drug release profile of the particles or of the composites is conferred.

Thus, for example, the invention contemplates a contact lens configured and arranged to cover a front extraocular surface, where a rim, or "carrier," of the contact lens would be either a silicon or silicon/polymer composite film impregnated with drug(s). The wearer would receive a sustained and monitorable release of drug through the contact lens.

Another preferred embodiment includes the use of episcleral plaques. An episcleral plaque is an extraocular way to deliver drugs and the intraocular dust Injection promotes monitoring of drug levels non-invasively. The invention contemplates use of a silicon or silicon/polymer composite film impregnated with drugs to be affixed or adhered to a retrobulbar surface of the eye. The patient would thereby receive a sustained and monitorable release of drug through the episcleral plaque.

While the invention is contemplated for use with a virtually unlimited number of pharmaceutical candidates, several exemplary drugs will be discussed herein.

For example, drug delivery for drugs used in treating ARMD and uveitis will be shown for purposes of illustration. These diseases require prolonged intraocular therapeutic drug levels to halt the progress of the disease and the deterioration of eyesight. However, the promising drugs for treating these diseases all share a common problem, which is the transient intraocular therapeutic level requires frequent intravitreal injections. These promising drugs include angiostatic steroids, metalloproteinase inhibitors, VEGF binding drugs, PEDF, an 8-mer peptide fragment of urokinase (uPA) and dexamethasone. In particular, PEDF, the 8-mer peptide fragment of uPA and dexamethasone all have short intravitreal half lives.

Either silicon smart dust or the episcleral one-way releasing plaque of biodegradable polymer imprint of silicon smart dust provide a device and method for intravitreal drug delivery that promotes sustained intraocular therapeutic drug levels with minimal invasiveness and elimination of systemic side effects.

Impregnation of the porous material may proceed in several ways. First, the candidate drug may be "physically" trapped within the pores, or second, the pores themselves may be chemically modified to bind the candidate drug.

Figure 1:
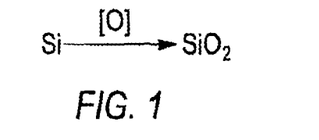
FIG. 1 represents a chemical reaction for the oxidation of the porous Si around a candidate molecule according to one embodiment of the invention.

More specifically, "physical trapping" is similar to building a ship in a bottle, where the "ship" is the candidate drug and the "bottle" is the nanometer-scale pores in the porous Si matrix. Small molecules can be trapped in the porous matrix by oxidizing the porous Si around the molecule. The relevant reaction is illustrated in FIG. 1, where "O" in the above equation is a molecular oxidant such as $O_2$, dimethyl sulfoxide, hydrogen peroxide, or water. Since oxidation of silicon adds two atoms of oxygen per atom of Si to the material, there is a significant increase in volume of the matrix upon oxidation. This has the effect of swelling the pore walls and shrinking the free volume inside the pores, and under the appropriate conditions, molecules present in the pores during oxidation become trapped in the oxide matrix.

The free volume in a porous Si film is typically between 50 and 80%. Oxidation should reduce this value somewhat, but the free volume is expected to remain quite high. Most of the current drug delivery materials are dense solids and can only deliver a small percentage of drug by weight. The amount of drug that can be loaded into the porous Si material is expected to be much larger than, for example, surface-modified nanoparticles or polylactide (PLA) polymers. Experiments can quantify the amount of each of the drugs that can be loaded into the smart dust delivery vehicle.

Figure 2:
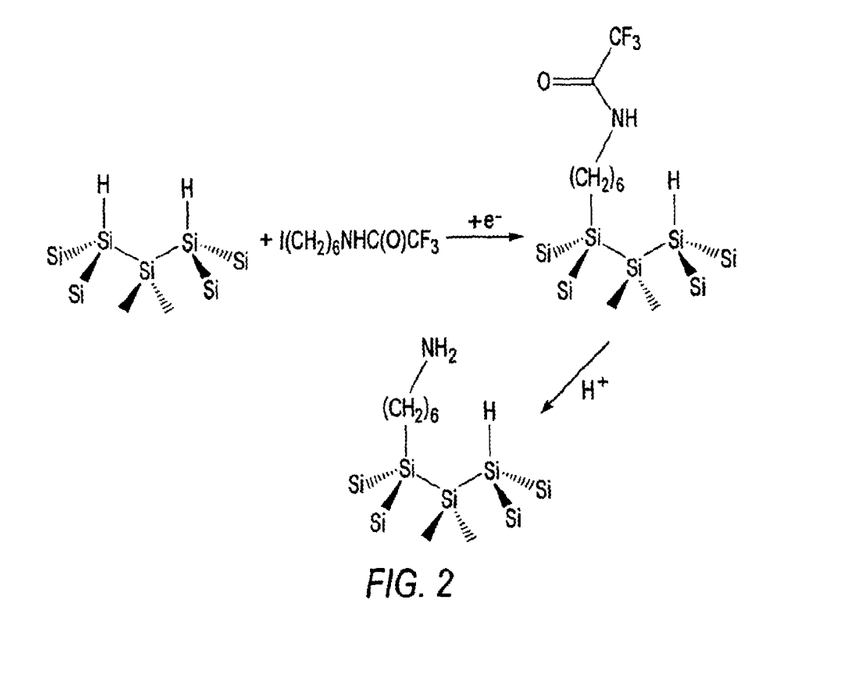
FIG. 2 illustrates a chemical modification reaction whereby a candidate molecule is attached to an inner pore wall according to another embodiment of the invention.

During chemical modification, a molecule is attached to the inner pore walls via covalent bonds. The inner pore walls can be configured to be chemically modified by one of the group consisting of functional alkenes, silicone oxide, functional organohalides, and metals. In the porous Si system, proteins, DNA, and various small molecules can be attached following several different procedures. The preferred embodiment uses electrochemical modification. For example, reduction of 1-iodo-6-(trifluoroacetylamino) hexane at a p-type porous silicon cathode leads to attachment of the trifluoroacetamidohexyl group. Subsequent acid-catalyzed hydrolysis should lead directly to the surface-bound amine species. The reactions are represented by the equation illustrated in FIG. 2.

The surface amine can then be functionalized with the 8-mer peptide fragment of uPA using standard peptide coupling methods.

Figure 3:
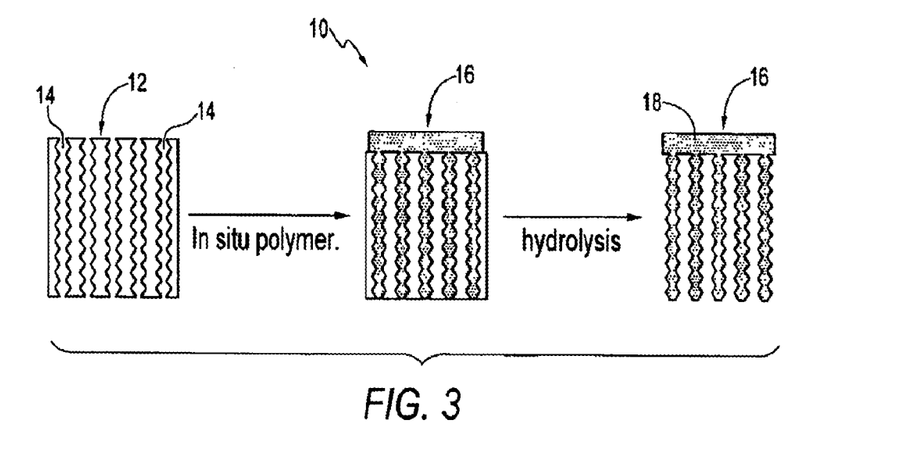
FIG. 3 is a schematic diagram illustrating a templated synthesis of polymer photonic crystals using porous Si masters according to a first embodiment of the invention.
Figure 4:
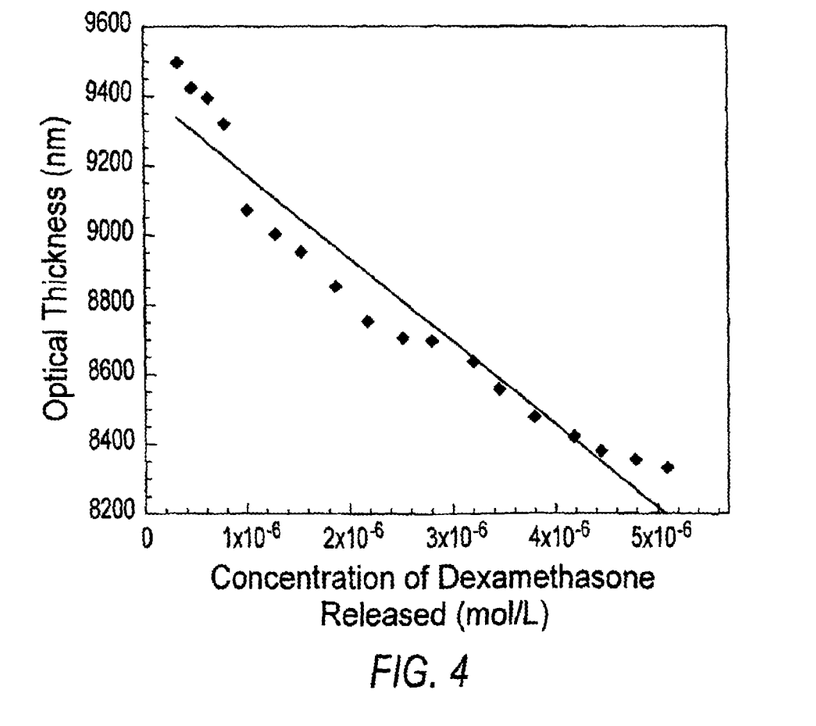
FIG. 4 is a graph illustrating a. correlation between the optical thickness of an alkylated porous silicon film to the concentration of drug appearing in phosphate buffered-saline solution over 2 hours.

The polymer replicas can be implanted on the sclera for trans-scleral drug release. It has been shown in rabbit eyes that polymer replicas are biocompatible and may safely and effectively remain in the eye for multiple months, if not years. Measurement of the decay in intensity of the peaks in the photonic crystal spectrum should provide a monitor of the rate of drug release from an implanted biocompatible polymer. In order to test the above hypothesis, drug-impregnated poly(L-lactide) (PL) films, cast from thermally oxidized porous silicon templates, can be prepared following a scheme, designated generally at 10, illustrated in FIG. 3. Specifically, a template (such as electropolished PSi), generally at 12, is provided, having pores 14 dimensioned to suit a particular application. A polymer, generally at 16, is loaded into the pores 14 to form a polymer-template composite. The template 12 is subsequently removed, leaving a polymer-based photonic film 16.

Replication of the optical spectrum in the biocompatible polymer upon removal of the porous silicon template can be used to confirm the replication process. The release characteristics of the polymers can be studied.

The degradation of the photonic structure in these films can be characterized in pH 7.4 aqueous buffer solutions, in vitro and in vivo. In accelerated degradation studies, we previously studied PL imprints impregnated with caffeine. We found that the intensity of the rugate peak displays an approximately exponential decay when the polymer is dissolved in pH 10 buffer. Simultaneous measurement of the decay of the spectral peak and the appearance of caffeine in the solution (caffeine absorption feature at 274 nm) confirmed that the drug was released on a time scale comparable to polymer degradation.

Embodiments of the invention also contemplate vectorial drug delivery. The polymer-based photonic film shown in FIG. 3 contains a polymer "cap" 18 on one side of the film. Films prepared in this manner will preferentially leach drug out one side of the film, allowing greater control of the drug delivery parameters. Manufacturing variables are channel sizes and packing.

Insofar as the invention contemplates including a virtually unlimited number of drugs, in vitro pharmacokinetic studies can be used to determine the appropriate configuration of the porous silicon film and its dust for each drug. The drug conjugated porous silicon film and its dust can be aliquoted into vitreous samples in cell culture dishes. Intensity of reflected light from the porous silicon film or its dust can be measured using a low power spectrophotometer, at the same time free drug in the vitreous sample can be measured, as a function of time for the porous film or dust immersed in the vitreous sample. Correlation between spectrophotometer change and drug concentration in vitreous can be determined and used for in vivo PK studies.

For biocompatible polymer imprints of the porous silicon film, drug can be impregnated in the polymer casting solution. Then the free standing polymer porous film can further conjugate with drug molecules to fill the pores. In vitro PK studies can be performed in a similar way as with the porous silicon film or its dust.

Optimized porous silicon smart dust adapted to the drug candidate will not be toxic after intravitreal injection and the vitreous drug half-life will be in the range of weeks and the drug level will sustain above the EC for months.

A preferred method includes preparing porous Si photonic crystal particles, loading the pores of those crystal particles with one or more drugs, and injecting the particles into the vitreous via syringe. The amount of drug loaded in the particles may then be monitored via one or more of a plurality of methods, such as by visual inspection, digital imaging, laser eye scan, or spectroscopic observation. Any of these four methods are non-invasive, allowing the practitioner or clinician to observe the particles through the pupil of the eye.

More particularly, one preferred method of the invention proceeds as follows. Porous Si photonic crystals are formed from a porous silicon film that is electrochemically etched in a single crystal Si substrate by application of a sinusoidal current density-time waveform. The waveform varies between 15 and 45 $mA/cm^2$, with 70 repeats and a periodicity of 12.5 s. The one-dimensional photonic crystal that results has a color that depends on the waveform parameters. The conditions described above produce a film that has a strong reflectivity maximum in the green region of the spectrum. This is a convenient color for visual observation in the eye, though any color or pattern of colors (multiple spectral peaks) can be incorporated into the films. The spectral features can range in wavelength from 300 nm to 10,000 nm. The film is removed from the Si substrate using a pulse of current. Particles with dimensions in the range 1 μm to 270 μm are generated by ultrasonication.

The photonic crystals are then loaded with a drug or drugs. The pores of the photonic crystlas are large enough to allow infiltration of small drugs such as dexamethasone. Drug can be loaded into the film or particles by infiltration from solution. In a typical preparation, the drug loading solution consisted of 6.times.10-2 M dexamethasone in methanol. 25 μL of the solution was pipetted onto the porous Si film and the solvent was allowed to evaporate in air. The film was briefly rinsed with deionized water to remove any excess drug remaining on the surface that had not infiltrated the pores.

Once the drug is loaded into the pores of the photonic crystals, the photonic crystals are then injected into the patient. The drug-loaded crystals are placed in an appropriate excipient and injected into the vitreous. After intravitreal injection, the porous silicon particles floated in the vitreous affording an ophthalmoscopically clear view of the fundus without any observed toxicity. The particles may last in the vitreous for up to four months without any noticeable abnormalities.

The optical interference spectrum used in particle identification can readily be measured with inexpensive and portable instrumentation such as a CCD spectrometer or a diode laser interferometer. Removal of the drug from the porous nanostructure results in a change in. the refractive index of the porous film and is observed as a wavelength shift in the spectrum, or a shift in the code, of the dust particle. The high surface area and optical interferometric means of detection lead to very high sensitivity for this system. Furthermore, particles can be encoded to reflect infrared light that can penetrate living tissues and enable noninvasive sensing through opaque tissue.

Experimental Data and Results:

Porous silicon dust was injected into rabbit vitreous and no toxicity was found compared with the fellow eyes that received the same volume of phosphate-buffered saline (PBS) injection. The porous silicon film was etched using a sinusoidal current varying between 15 and 45 mA/cm$^2$, with 70 repeats and a periodicity of 12.5 s. The film was sonicated into a dust that ranged from 1 µm to 270 µm. After intravitreal injection, the porous silicon particles floated in the vitreous affording an ophthalmoscopically clear view of the fundus without any observed toxicity. The particles lasted in the vitreous for one week without any noticeable abnormalities.

Thermally oxidized silicon dust was also injected into the vitreous of four rabbits. This chemical modification of the porous silicon film was proposed as one of the alternative methods to increase the residence time of the porous silicon dust in vitreous. This approach demonstrated a great increase of the residence time of the particles in the rabbit eye compared to the previous incompletely hydrosilylated smart dust (from less than 7 days to longer than 3 weeks). In addition, by increasing the sonication time during preparation, smaller and more uniform smart dust particles were produced, which can be delivered into vitreous by the 25 or 27-gauge needle that is commonly used for intravitreal injection in the clinic.

Additional data supports use of completely hydrosilated porous Si photonic crystals that have no toxicity by clincial examination or electroretinograms or histology at 3½ months post injection, inclusive of shorter times. For example, 100 microliters of the material were injected, and the characteristic color of the crystals is seen making it clear that one can use this characteristic for monitoring drug release in the eye.

Intravitreal injection of 100 µl of oxidized porous Si photonic crystal particles in 5% dextrose was performed. The measured size of the smart dust ranged from 10 to 45 µm with an average of 30 µm; approximately 30,000 particles were injected into each rabbit eye. The injected particles appeared purplish green floating in the vitreous. From the second day some of the particles aggregated and sank onto the inferior retina. No toxicity was seen and the smart dust particles were still visible at the last examination 34 weeks later with at least half of the originally injected material remaining, as assessed by ophthalmoscopy. It is therefore anticipated that the particles would be safe and effective for at least a year if not two years. Thus, this preliminary thermal oxidation modification has greatly extended the time of intravitreal residence compared to the previous incompletely hydrosilylated smart dust.

The data demonstrated that the porous silicon particle was safe as an intravitreal drug delivery vehicle. Modifications such as oxidation and silicon-carbon chain conjugation can be used to further increase the stability of the silicon dust and can make it a long-lasting slow release intravitreal drug delivery system.

A preliminary study was performed on a rat CNV model using systemic administration of an 8-mer peptide derived from urokinase plasminogen activator (uPA) to block the uPA-urokinase plasminogen activator receptor (uPAR) interaction. This 8-mer peptide was administrated subcutaneously twice daily at 200 mg/kg/d beginning at the time of induction of CNV (with laser) to introduce CNV in Brown Norway rats. Two weeks after laser treatment, simultaneous FA and ICG using scanning laser angiography was performed to identify the leaking laser burns. The results showed that this 8-mer peptide reduced the laser induced CNV by 70% compared to the control group (44.7% of laser burns leak in control group versus 13.4% in treated group, p<0.001). [55] Administration of the drug intravitreally using a proposed porous silicon smart dust should maintain the desired intraocular drug level.

Thermal Oxidation of Porous Si Particles

Preliminary studies of porous Si particles oxidized and annealed at 300° C. for 2 hours in air show that the material is stable in aqueous pH 11 buffer for several days, and recent results indicate that this approach can dramatically increase the residence time of the particles in the rabbit eye. In addition, by increasing the sonication time during preparation, smaller and more uniform smart dust particles were produced which can be delivered into vitreous by the 28.5 gauge needle that is commonly used for intravitreal injection in the clinic. Intravitreal injection of 100 µl of oxidized porous Si photonic crystal particles in 5% dextrose was performed. The measured size of the smart dust ranged from 10 to 45 µm with a average of 30 µm; approximately 30,000 particles were injected into each rabbit eye. The color of the injected particles floating in the vitreous was clearly visible, which is indicative of drug release and degradation by hydrolysis. Degradation by hydrolysis is especially advantageous in that no enzymes are necessary to degrade the particles. From the second day some of the particles aggregated and sank onto the inferior retina. No toxicity was noticed and the smart dust particles were still visible until the last examination, which indicates that this preliminary thermal oxidation has more than tripled the time of intravitreal residence compared to the previous incompletely hydrosilylated smart dust. Experiments can be performed to quantify the residence time and correlate it with tile chemical modification conditions such as thermal oxidation time, temperature, and ambient atmosphere.

Electrochemical Grafting of Organic Reagents

The hydride-terminated surface of p-type or p$^{++}$-type porous silicon can be stabilized by electrochemical reduction of acetonitrile solutions of various organo halides. Reduction of 6-iodo-ethylhexanoate, 1-iodo-6-(trifluoroacetylamino) hexane, iodomethane, 1-bromohexane, or ethyl 4-bromobutyrate at a porous Si cathode results in removal of the halogen and attachment of the organic fragment to the porous Si surface via a Si—C bond. A two-step procedure was devised involving attachment of the functional group of interest followed by attachment of methyl groups (by reduction of iodomethane) to residual, more sterically inaccessible sites on the porous Si surface and found that electrochemical alkylation greatly improves the stability of porous Si against oxidation and corrosion in various corrosive aqueous media, and that the methyl capping procedure provides the most stable porous Si material yet reported. This chemistry also allows covalent attachment of the candidate drugs for the release studies.

Thermal Hydrosilylation of Organoalkenes

This approach provides a porous Si material that is stable even in boiling aqueous pH 10 solutions. This chemistry was extended to the dust particles and find similar levels of stability. Parameters of the reaction may be adjusted in order to identify the key parameters leading to this instability. In particular, the surface coverage (essentially the efficiency of the chemical reaction), the type of organic species grafted to the surface (alkyl carboxylates, alkyl esters, and alkyl halides), and the chain length of the alkyl species can be investigated. Reaction conditions such as the presence of added radical initiators, transition metal catalysts, and photoassisted hydrosilylation can be explored.

For each modified porous silicon film, its sonicated dust can be intravitreally injected into 3 rabbit eyes with the fellow eyes used for control. After injection, the toxicity can be monitored by slit lamp, indirect ophthalmoscope, ERG, and pathology. In addition, a remote spectrometer probe can be used to determine the clearance rate of the silica dust in vitreous on living animals through the dilated pupil. The spectrometer probe is believed to render more accurate information since the small particles may not be seen using indirect ophthalmoscope.

A spectrometric method of detection of the oxidized "smart dust" injected into the rabbit eyes was also investigated. One eyepiece of the surgical microscope was connected to the input of a fiber-optic based spectrophotometer and this allows us to accurately focus the detecting light on the intraocular "smart dust" particles. The preliminary data showed a feasibility of this approach and the specific wavelength of a porous Si photonic film was detected with a 1 nm spectral resolution. This resolution is sufficient to determine concentration of a species such as a large protein in the porous Si film to micromolar concentration levels. As an alternative, the probe can be adapted to a fundus camera which is used for clinical retinal imaging. For the rabbit or rodent eyes, the fundus can be photographed using a fundus camera without anesthesia.

In in vitro experiments, the optical codes of the porous Si photonic crystal particles can be read using digital imaging cameras. Since the color of the particles provides an indirect measure of the amount of drug loaded, the most accurate measure is obtained using a spectrometer. However, the color resolution in a digital camera is sufficient to measure the loading to an accuracy of 10%, which is sufficient for the present application. In order to measure the degree of loading in porous Si "smart dust," the color of the particles can be recorded using a color digital camera connected to the fundus camera. Software to process the digital images and extract concentration information can be obtained with minor modifications to commercially available software. The advantage of this approach is that it requires only minor modification to existing readily available medical equipment, and it allows acquisition of data from a large number of particles simultaneously. If higher resolution concentration information is needed, the illumination light can be filtered using a monochromator or bandpass filters, providing spectral resolution equivalent to that which can be obtained with a spectrometer.

The long-lasting porous silicon film and its imprint can be further optimized for delivery of three candidate drugs (PEDF, an 8-mer peptide fragment of uPA, and dexamethasone) by controlling the pore size and morphology. These parameters are easily controlled using the appropriate anodic electrochemical etching current density, duration of the etch cycle, and etchant solution composition. Since the imprint and its porous silicon template share the similar nanostructures, it is assumed that imprints from optimized porous silicon can also be appropriate for delivering those drug candidates.

Additional in vivo data regarding the "smart dust" material after intraocular injection and new in vitro data concerning the release of dexamethasone from "smart dust" formulations is as follows.

In vivo Studies

The new formulation of "smart dust" particles containing a silicon dioxide shell have been observed in the vitreous of living rabbits for 16 weeks and they are showing evidence of dissolution without any evidence of toxicity by slit lamp, indirect ophthalmoscopic examinations or by light or electron microscopy. More than half of the particles appear to be present at this time point indicating excellent potential as a long acting drug delivery system. Injection of "smart dust" particles containing a hydrosilylated alkyl shell into the living rabbit eye has shown no evidence of toxicity for up to five weeks of ongoing examination.

Additional in vivo studies demonstrated the increased stability of "smart dust" particles containing a hydrosilylated alkyl shell. These chemically modified particles also exhibit slower release rates for a drug. Release of dexamethasone from the modified porous silicon matrix is slowed by a factor of 20 compared to unmodified porous silicon.

Chemistries have also been developed to expand the pores in order to accommodate larger molecules within the pores, such as a modified Fab fragment of human IgG. The pore expansion procedure involves the enlargement of pores by treatment with dimethylsulfoxide (DMSO) containing hydrofluoric acid (HF). The porosity increases approximately 10% after the expansion treatment, and it was found that this chemistry allows admission of large molecules such as human IgG (150 kDa) and bovine serum albumin (67 kDa).

As will be clear to artisans, the invention makes use the optical properties of porous silicon photonic crystals to monitor drug delivery rates. The shift in the reflectivity spectrum of the film coincides with release of a drug. Optical measurements were carried out while concurrent absorbance measurements were obtained as the drug-infused porous silicon films were introduced in buffered aqueous solutions. There is a linear correlation between the increase of drug concentration in solution (i.e. drug diffusing from the pores) and a change in the optical thickness of the porous silicon film.

While various embodiments of the present invention have been shown and described, it should be understood that modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. A method for treating an intraocular disease of the eye comprising administering to an eye of a patient a porous silicon dioxide particle having pores comprising a drug for treatment of the disease, thereby delivering the drug to the eye.

2. The method of claim 1, wherein the porous silicon dioxide particle has a dimension of from 1 μm to 270 μm.

3. The method of claim 1, wherein the porous silicon dioxide particle has a dimension of from 10 μm to 45 μm.

4. The method of claim 1, wherein the porous silicon dioxide particle has a free volume of from 50% to 80% based on the total volume of the porous silicon dioxide particle.

5. The method of claim 1, wherein the administering comprises injection.

6. The method of claim 5, wherein the administering comprises intravitreal injection.

7. The method of claim 1, wherein the drug is a protein or peptide.

8. The method of claim 7, wherein the protein or peptide is selected from the group consisting of pigment epithelium derived factor (PEDF), and an 8-mer peptide fragment of urokinase (uPA).

9. The method of claim 1, wherein the drug is dexamethasone.

10. The method of claim 1, wherein the drug is a nucleic acid.

11. The method of claim 1, wherein the intraocular disease comprises glaucoma, age-related macular degeneration (ARMD), choroidal neovascularization (CNV), or uveitis.

* * * * *